United States Patent
Bischof

(10) Patent No.: US 6,361,692 B1
(45) Date of Patent: *Mar. 26, 2002

(54) ON LINE BLOOD PROCESSING SYSTEM FOR OBTAINING FOR STORAGE A BLOOD SUSPENSION HAVING A REDUCED RESIDUAL LEUKOCYTE POPULATION

(75) Inventor: Daniel F. Bischof, McHenry, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/548,190

(22) Filed: Apr. 13, 2000

Related U.S. Application Data

(62) Division of application No. 09/223,212, filed on Dec. 30, 1998, now Pat. No. 6,051,147, which is a division of application No. 08/606,189, filed on Feb. 23, 1996, now Pat. No. 5,865,785.

(51) Int. Cl.$^7$ .................. B01D 36/00; B01D 21/26; A61M 37/00
(52) U.S. Cl. .............. 210/252; 210/257.1; 210/258; 210/416.1; 210/782; 210/787; 210/789; 210/767; 494/36; 494/37; 604/4.01; 604/6.01; 604/6.03; 604/6.11
(58) Field of Search ................ 210/782, 787, 210/789, 767, 252, 257.1, 258, 416.1; 494/36, 37; 604/4.01, 6.01, 6.03, 6.11

(56) References Cited

U.S. PATENT DOCUMENTS

| | | |
|---|---|---|
| 4,025,618 A | 5/1977 | Garber et al. |
| 4,701,267 A | 10/1987 | Watanabe et al. ............ 604/5 |
| 4,915,683 A | 4/1990 | Sieber |
| 4,985,153 A | 1/1991 | Kuroda et al. ............ 210/782 |
| 5,023,052 A | 6/1991 | Nagatoma et al. ............ 422/56 |
| 5,089,146 A | 2/1992 | Carmen et al. |
| 5,100,564 A | 3/1992 | Pall et al. |
| 5,102,407 A | 4/1992 | Carmen et al. ............ 604/410 |
| 5,229,012 A | 7/1993 | Pall et al. |
| 5,288,403 A | 2/1994 | Ohno |
| 5,298,165 A | 3/1994 | Oka et al. ............ 210/645 |
| 5,300,019 A | 4/1994 | Bischof et al. |
| 5,387,187 A | 2/1995 | Fell et al. ............ 604/46 |
| 5,399,268 A | 3/1995 | Pall et al. |
| 5,403,272 A | 4/1995 | Deniega et al. ............ 604/6 |
| 5,494,592 A | 2/1996 | Latham, Jr. et al. ......... 210/782 |
| 5,498,336 A | 3/1996 | Katsurada et al. .......... 210/496 |
| 5,501,795 A | 3/1996 | Pall et al. |
| 5,512,187 A | 4/1996 | Buchholz et al. |
| 5,536,238 A | 7/1996 | Bischof ......................... 604/6 |
| 5,545,339 A | 8/1996 | Bormann et al. ........... 210/782 |
| 5,545,516 A | 8/1996 | Wagner |
| 5,549,834 A | 8/1996 | Brown .......................... 604/6 |
| 5,591,337 A | 1/1997 | Lynn et al. ................. 210/489 |
| 5,607,579 A | 3/1997 | Latham, Jr. et al. .......... 210/85 |
| 5,865,785 A | 2/1999 | Bischof ........................ 494/35 |

Primary Examiner—John Kim
(74) Attorney, Agent, or Firm—Daniel D. Ryan; Bradford R. L. Price; Michael C. Mayo

(57) ABSTRACT

Blood processing systems and methods establish on line communication between a container and a source of blood containing leukocytes and platelets, such as a human donor. The systems and methods create a centrifugal field between the source of blood and the container that separates from the blood an unfinished suspension of platelets having a first physiologic characteristic different than the desired physiologic characteristic. The systems and methods pump the unfinished platelet suspension outside the centrifugal field through a finishing device. The finishing device changes the first physiologic characteristic to the desired physiological characteristic, thereby creating the finished platelet suspension. The systems and methods convey the finished platelet suspension from the finishing device directly into the container. The systems and methods function without interrupting the on line communication between the container and the source of blood.

4 Claims, 2 Drawing Sheets

ON LINE BLOOD PROCESSING SYSTEM FOR OBTAINING FOR STORAGE A BLOOD SUSPENSION HAVING A REDUCED RESIDUAL LEUKOCYTE POPULATION

This is a divisional of application(s) Ser. No. 09/223,212 filed on Dec. 30, 1998, now U.S. Pat. No. 6,051,147, which is a division of Ser. No. 08/606,189, filed on Feb. 23 1996 (now U.S. Pat. No. 5,865,785).

FIELD OF THE INVENTION

The invention generally relates to blood processing systems and methods. In a more specific sense, the invention relates to systems and methods for removing leukocytes from blood components collected for therapeutic purposes.

BACKGROUND OF THE INVENTION

Today blood collection facilities routinely separate whole blood into its various therapeutic components, such as red blood cells, platelets, and plasma.

One separation technique that is in widespread use today uses a multiple blood bag system. The bag system includes a primary blood bag and one or more transfer bags, which are integrally connected to the primary bag by tubing. The technique collects from a donor a single unit (about 450 ml) of whole blood in the primary blood bag. The donor is then free to leave.

The donor's whole blood later undergoes centrifugal separation within the primary bag into red blood cells and plasma rich in platelets. The plasma rich in platelets is expressed out of the primary bag into a transfer bag, leaving the red blood cells behind. The plasma rich in platelets then undergoes further centrifugal separation within the transfer bag into a concentration of platelets and plasma poor in platelets. The plasma poor in platelets is expressed from the transfer bag into another transfer bag, leaving the concentration of platelets behind.

Using multiple blood bag systems, all three major components of whole blood can be collected for therapeutic use. However, the yield for each component collected is limited to the volume of the components that are contained in a single unit of whole blood. Furthermore, because red blood cells are retained, United States governmental regulations prohibit collecting another unit of whole blood from the donor until six weeks later.

Certain therapies transfuse large volumes of a single blood component. For example, some patients undergoing chemotherapy require the transfusion of large numbers of platelets on a routine basis. Multiple blood bag systems simply are not an efficient way to collect these large numbers of platelets from individual donors.

On line blood separation systems are today used to collect large numbers of platelets to meet this demand. On line systems perform the separation steps necessary to separate concentration of platelets from whole blood in a sequential process with the donor present. On line systems establish a flow of whole blood from the donor, separate out the desired platelets from the flow, and return the remaining red blood cells and plasma to the donor, all in a sequential flow loop.

Large volumes of whole blood (for example, 2.0 liters) can be processed using an on line system. Due to the large processing volumes, large yields of concentrated platelets (for example, $4 \times 10^{11}$ platelets suspended in 200 ml of fluid) can be collected. Moreover, since the donor's red blood cells are returned, the donor can donate whole blood for on line processing much more frequently than donors for processing in multiple blood bag systems.

Regardless of the separation technique used, when collecting blood components for transfusion, it is desirable to minimize the presence of impurities or other materials that may cause undesired side effects in the recipient. For example, because of possible febrile reactions, it is generally considered desirable to transfuse red blood cells and platelets that are substantially free of leukocytes, particularly for recipients who undergo frequent transfusions.

Several United States Patents are directed to the removal of leukocytes from red blood cells and platelet components in multiple blood bag systems. For example, see U.S. Pat. Nos. 4,767,541; 5,089,146; 5,100,564; and 5,128,048.

U.S. Pat. No. 5,427,695 is directed to the removal of leukocytes from platelet-rich plasma during on line blood processing.

The platelet-rich suspension product obtained using prior on line blood collection systems and methods may still lack the desired physiologic characteristics imposed by the end user (typically a blood bank or hospital) for long term storage and transfusion. For example, the platelet-rich suspension may include residual leukocytes that, while very small in relation to the leukocyte population in whole blood, are still greater than the leukocyte population standards desired by the end user.

Therefore, despite significant advances in blood processing technology, a need still exists for further improved systems and methods for removing undesired matter like leukocytes from blood components in a way that lends itself to use in high volume, on line blood collection environments.

SUMMARY OF THE INVENTION

The invention provides on line blood processing systems and methods for obtaining a finished platelet suspension having a desired physiologic characteristic. In a preferred embodiment, the desired physiologic characteristic comprises a desired reduced residual population of leukocytes.

The systems and methods that embody features of the invention establish on line communication between a container and a source of blood containing leukocytes and platelets, such as a human donor. The systems and methods create a centrifugal field between the source of blood and the container. The centrifugal field separates from the blood an unfinished suspension of platelets having a first physiologic characteristic different than the desired physiologic characteristic. In a preferred embodiment, the unfinished platelet suspension contains an initial leukocyte population greater than the desired residual leukocyte population.

According to the invention, the systems and methods pump the unfinished platelet suspension outside the centrifugal field through a finishing device. The finishing device changes the first physiologic characteristic to the desired physiological characteristic, thereby creating the finished platelet suspension. In a preferred embodiment, the finishing device reduces the leukocyte population by filtration. The systems and methods convey the finished platelet suspension from the finishing device directly into the container for storage or transfusion.

The systems and methods that embody the features of the invention function without interrupting the on line communication between the container and the source of blood.

Other features and advantages of the invention can be found in the drawings, accompanying description, and claims of this Specification.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
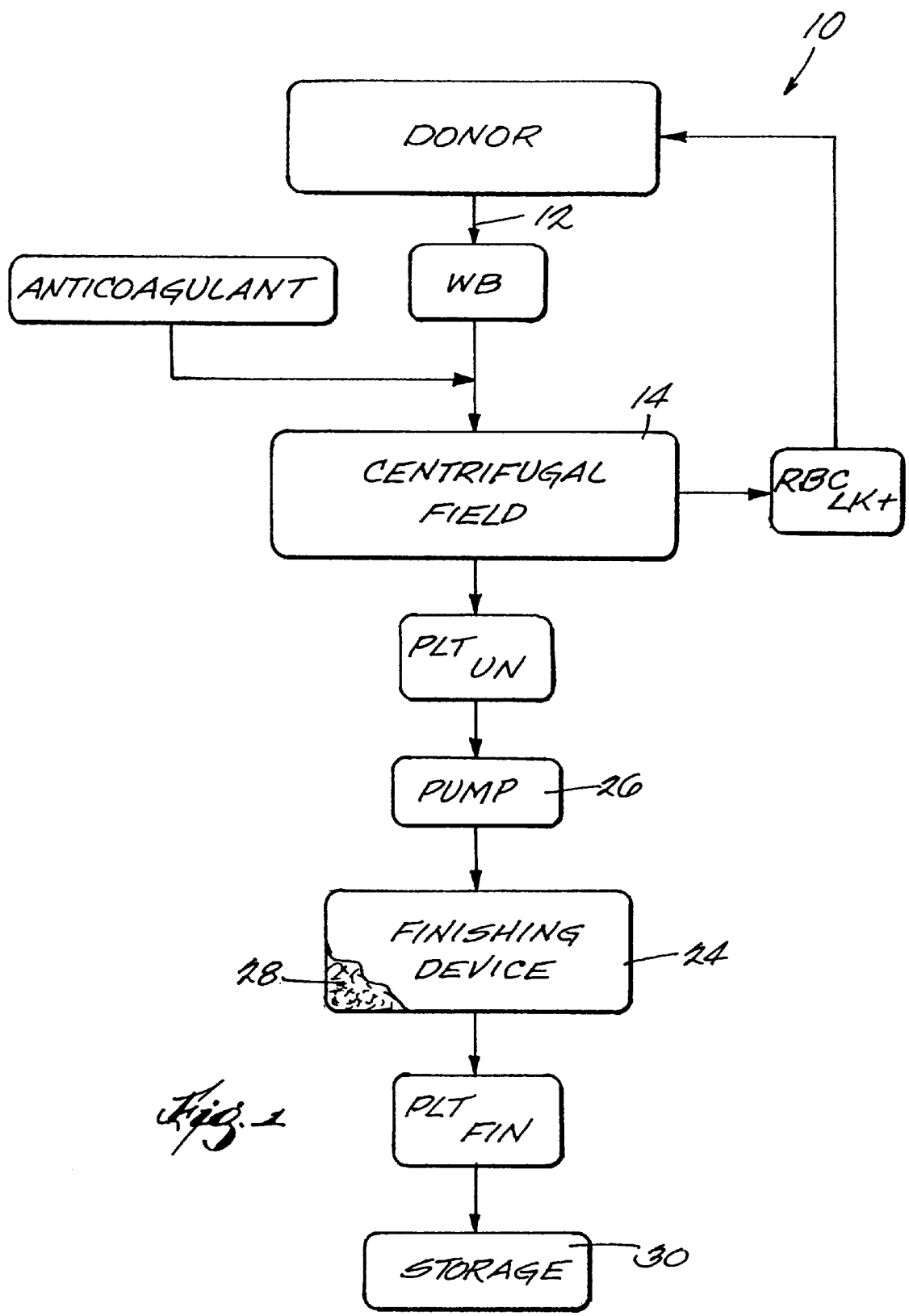
FIG. 1 is a diagrammatic view of a blood processing system, which includes a finishing device that embodies the features of the invention.

FIG. 1 shows in diagrammatic form an on line blood processing system 10 that embodies features of the invention. According to the invention, the on line system 10 provides a finished, high quality platelet-rich blood product ($PLT_{FIN}$), with a significantly reduced residual population of leukocytes and/or other enhanced physiological properties, suited for long term storage and transfusion.

As used in this Specification, the term "on line blood separation process" refers to a blood separation system or method that (i) establishes communication between a blood source (typically, a human blood donor) and an extracorporeal flow path; (ii) draws a blood volume from the donor into the flow path; and (iii) maintains communication with the circulatory system of the donor for at least a portion of the time that the blood volume undergoes separation within the extracorporeal flow path.

As used in this Specification, an "on line blood separation process" can separate the blood volume either in a continuous manner or in an interrupted manner. However, an "on line blood separation process" maintains communication between the flow path and the donor for at least a portion of the time the separation process occurs within the flow path, regardless of specific timing or sequencing of the separation process itself.

As used in this Specification, an "on line blood separation process" can include external or internal valves or clamps to interrupt flow within the path to or from the donor. However, in the context of this Specification, such valves or claims do not break the communication between the blood donor and the flow path. Instead, the valves or clamps control fluid flow within the path while maintaining communication between it and the blood donor.

The on line system 10 draws whole blood (WB) from a donor through a phlebotomized tubing flow path 12. WB contains, as its principal components, red blood cells, platelets, leukocytes, and plasma. The system 10 adds anticoagulant to the drawn WB and conveys anticoagulated WB into a centrifugal field 14 for processing.

In the centrifugal field 14, the system 10 ultimately separates anticoagulated WB into two components. The first component is a red blood cell concentration. It is desirable that the red blood cell concentration also carry with it a majority of the leukocyte population (LK) present in the WB. For this reason, the first component is referred to as $RBC_{LK+}$.

$RBC_{LK+}$ is returned to the donor during processing. This avoids depletion of the donor's red blood cell and leukocyte populations while high volume yields of platelets are obtained.

The second component comprises an unfinished platelet-rich plasma suspension $PLT_{UN}$. $PLT_{UN}$ is considered "unfinished" because the platelet-rich plasma suspension still lacks the desired physiologic characteristics imposed by the end user (typically a blood bank or hospital) for long term storage and transfusion. Centrifugal processing within the field 14 often cannot provide these desired characteristics.

The specific physical makeup of the platelet-rich suspension comprising $PLT_{UN}$ can vary. The makeup will largely depend upon the efficiency of the centrifugal separation process in terms of the how many platelets are separated (i.e., the platelet yields) and how much platelet-poor plasma product is withdrawn and not returned to the donor.

As used in this Specification, $PLT_{UN}$ is intended to encompass any suspension in which platelets are present in concentrations greater than in whole blood. $PLT_{UN}$ can comprise what is commonly referred to as platelet-rich plasma (PRP) or platelet concentrate (PC), or suspensions of platelets and plasma lying in between.

$PLT_{UN}$ can include, in addition to platelets, other components or ingredients, depending upon the choice of the end user. For example, $PLT_{UN}$ can include essentially only plasma as the platelet suspension media. Alternatively or in addition to plasma, $PLT_{UN}$ can include a specially formulated platelet storage media to suspend the platelets.

The structural details of the centrifugation field 14 can vary and are not essential to the invention. For example, the field 14 can comprise a centrifuge and multiple stage centrifugal processing chambers of the type shown in Brown U.S. Pat. No. 5,427,695 or Brown U.S. Pat. No. 5,370,802, both of which are incorporated herein by reference.

Figure 2:
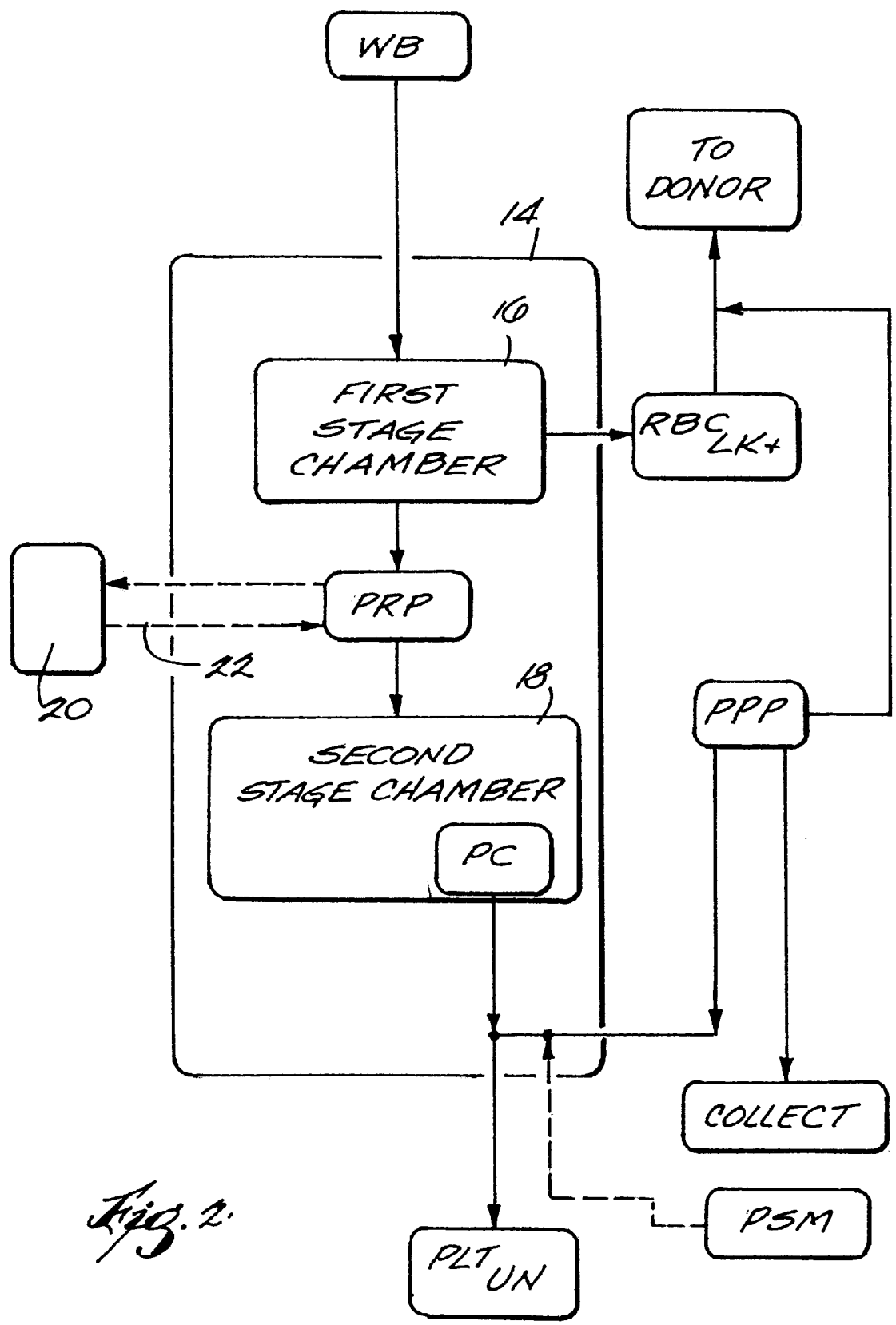
FIG. 2 is a diagrammatic view of a centrifugal blood processing system that can be use in association with the finishing device shown in FIG. 1.

As FIG. 2 shows in diagrammatic form, the multiple stage processing chambers that Brown '695 and '802 embody separate WB into RBC and PRP in a first stage separation chamber 16. The special fluid flow dynamics that occur in the first stage chamber 16 shown in Brown '802 or '695 keep a large majority of leukocytes out of PRP and with the RBC in the first stage chamber 16 for return to the donor as $RBC_{LK+}$. The special fluid flow dynamics occurring in the first stage chamber 16 in Brown '802 or Brown '695 also provide a high yield of platelets in the PRP.

In Brown '802 or '695, PRP is transported from the first stage chamber 16. A portion is recirculated back to the WB entering the first stage chamber 16, and the rest is conveyed into a second stage chamber 18. The PRP is separated in the second stage chamber 18 into PC and platelet-poor plasma (PPP).

PC retained in the second stage chamber 18 is later resuspended in a volume of PPP or (optionally) a suitable platelet storage medium for transfer from the second stage chamber as $PLT_{UN}$. A portion of the PPP is returned to the donor, while another portion of PPP is retained for use as a recirculation or keep-open or rinse-back or resuspension media, or for storage for fractionation or transfusion.

One reason why $PLT_{UN}$ can be considered "unfinished" in the context of the above described system is the presence of residual leukocytes in the platelet suspension. This residual population of leukocytes with the platelets, while small, still can be greater than the leukocyte population standards demanded by the end user.

Often, centrifugal processing alone often is not effective at isolating enough leukocytes from PRP to meet these demands. Unintended perturbations and secondary flows along the interface between RBC and plasma, where leukocytes reside, can sweep lighter leukocyte species away from RBC into the plasma. Other desirable flow patterns that sweep heavier leukocytes species in the interface back into the RBC mass can also fail to develop to their fullest potential. The dynamic processes under which leukocytes are separated from platelets during centrifugation are complex and subject to variation from donor to donor.

Additional steps can be provided to augment the primary centrifugal separation process to thereby reduce the number of residual leukocytes present in $PLT_{UN}$. For example, as disclosed in Brown '695, a leukocyte filter 20 can be provided after the first stage chamber 16 to filter leukocytes from PRP before entering the second stage chamber 18 for separation into PC and PPP. The filter 20 is preferably located outside the centrifugal field 14, being connected by a rotating umbilicus arrangement 22 of conventional construction. Alternatively, though, the filter 20 can be located within the centrifugal field 14.

Alternatively, or in combination with such other ancillary leukocyte-reduction devices, $PLT_{UN}$ can be subject to particle bed separation effects within the centrifugal field 14 to separate leukocytes from the platelets. Still, the degree of leukocyte reduction demanded by the user can exceed the capabilities of even these ancillary steps during the centrifugal separation process.

For this reason (see FIG. 1), the system 10 includes an in line finishing device 24 located outside the centrifugal field 14. A pump 26 conveys $PLT_{UN}$ under pressure from the centrifugal field 14 through the finishing device 24. In FIG. 1, the pump 26 is shown downstream of the centrifugal field 14. Alternatively, the pump 26 could be located upstream of the centrifugal field 14, thereby supplying the requisite machine pressure to convey $PLT_{UN}$ from the centrifugal field 14.

The finishing device 24 serves to affect a desired alteration in the makeup or physiological of $PLT_{UN}$ that could not be effectively achieved in the centrifugal field 14, such as, for example, a further incremental reduction in the leukocyte population. The in line finishing device 24 performs its function on line, while the donor remains connected in communication with the system 10.

The output of the finishing device 24 is a finished platelet-rich suspension($PLT_{FIN}$). $PLT_{FIN}$ is considered "finished" because the platelet-rich plasma suspension possesses the desired physiologic characteristics imposed by the end user for long term storage and transfusion. In the context of the illustrated embodiment, the platelet-rich suspension comprising $PLT_{FIN}$ possesses a more-reduced leukocyte population and/or additional physiological attributes not present in $PLT_{INI}$.

As used in this Specification, the term "reduced" or "more-reduced" does not denote that all the residual leukocytes have been removed. The term is intended to more broadly indicate only that the number of residual leukocytes have been incrementally reduced by the finishing device 24, compared with the number before processing by the finishing device.

The finishing device 24 can accomplish its function by centrifugation, absorption, columns, chemical, electrical, and electromagnetic means. In the illustrated and preferred embodiment, the finishing device 24 comprises a filter that employs a non-woven, fibrous filter media 28.

The composition of the filter media 28 can vary. The media 28 comprises fibers that contain nonionic hydrophillic groups and nitrogen-containing basic functional groups. Fibers of this type are disclosed in Nishimura et al U.S. Pat. No. 4,936,998, which is incorporated herein by reference. Filter media containing these fibers are commercially sold by Asahi Medical Company. Filter media containing these fibers have demonstrated the capacity to remove leukocytes while holding down the loss of platelets. Alternatively, the filter media 28 can comprise fibers that have been surface treated as disclosed in Gsell et al U.S. Pat. No. 5,258,127 to increase their ability to pass platelets while removing leukocytes. Gsell et al. U.S. Pat. No. 5,258,127 is also incorporated herein by reference.

Furthermore, because the pump 26 is used to convey $PLT_{INI}$ through the finishing device 24, the external machine pressure it creates can be used to overcome passive resistance of the finishing media 28. Therefore, the finishing media 28 can be densely packed within the finishing device 24 to achieve maximum efficiencies.

The system 10 conveys $PLT_{FIN}$ to one or more containers 30 suitable for transfusion or long term storage. The container(s) 30 intended to store $PLT_{FIN}$ can be made of polyolefin material (as disclosed in Gajewski et al U.S. Pat. No. 4,140,162) or a polyvinyl chloride material plasticized with tri-2-ethylhexyl trimellitate (TEHTM). These materials, when compared to DEHP-plasticized polyvinyl chloride materials, have greater gas permeability that is beneficial for platelet storage.

The system 10 shown in FIG. 1 can be readily incorporated into a continuous single or double needle on line blood processing systems.

As used in this Specification, the "on line blood separation process" differs from a multiple blood bag process. In a multiple blood bag process, the donor's circulatory system does not remain in communication with the flow path where separation of the collected blood volume occurs. In a multiple blood bag system, after a given blood volume is collected in the primary bag, the donor's circulatory system is disconnected from the primary bag before separation occurs within the bag. Also, in a multiple blood bag system, the separation processes do not occur continuously. The first stage separation of red blood cells and plasma rich in platelets and the second stage separation of platelets from plasma occur at different points in time as separate, discontiguous steps.

Various features of the inventions are set forth in the following claims.

I claim:

1. An on line blood processing system for obtaining for storage a blood suspension having a reduced residual leukocyte population comprising a tubing system operative for establishing on line communication between a storage container for the blood suspension and a source of blood containing leukocytes, a device communicating with the tubing system operative for creating, without interrupting the on line communication between the storage container and the source of blood when in use, a centrifugal field that generates separation forces to separate from the blood a first blood suspension having an initial population of leukocytes, a finishing device communicating with the tubing system outside the centrifugal field operative, in response to contact with the first blood suspension when in use, for reducing the initial leukocyte population in the first blood suspension, thereby creating a second blood suspension having a reduced residual leukocyte population less than the initial population of leukocytes, a pump communicating with the tubing system operative, without interrupting the on line communication between the storage container and the source of blood when in use, for pumping the first blood suspension outside the centrifugal field through the finishing device under pressure from the centrifugal field, and tubing communicating with the tubing system outside the centrifugal field operative, without interrupting the on line communication between the storage container and the source of blood when in use, for conveying the second blood suspension from the finishing device directly into the storage container without exposure to the separation forces of the centrifugal field.

2. A system according to claim 1 wherein the finishing element comprises a filter media.

3. An on line blood processing system for obtaining for storage a blood suspension having a reduced residual leukocyte population comprising a flow path operative for establishing on line communication between a storage container for the blood suspension and a source of blood containing leukocytes, a separation device communicating in line with the flow path between the source and the container to receive blood from the source, the separation device including a centrifugal separation element operative, without interrupting the on line communication between the container and the source of blood when in use, for creating a centrifugal field that generates separation forces to separate from the blood a first blood suspension having an initial population of leukocytes, a finishing device communicating in line with the flow path outside the centrifugal field, the finishing device including an inlet communicating with the separation device and an outlet communicating with the storage container and not the separation device, the finishing device including a finishing element operative, during passage of the first blood suspension between the inlet and outlet when in use, for reducing the initial leukocyte population in the first blood suspension to a reduced residual leukocyte population less than the initial population of leukocytes, and a pump in line with the flow path operative, without interrupting the on line communication between the flow path and the blood source when in use, for pumping the first blood suspension outside the centrifugal field through the finishing device inlet under pressure from the centrifugal field for passage through the finishing element, to thereby change the first blood suspension into a second blood suspension having the reduced residual leukocyte population, the pump also being operative when in use for pumping the second blood suspension from the finishing device outlet directly into the storage container without exposure to the separation forces of the centrifugal field.

4. A system according to claim 3 wherein the finishing element comprises a filter media.

* * * * *